(12) United States Patent
Heldal et al.

(10) Patent No.: US 10,695,721 B2
(45) Date of Patent: Jun. 30, 2020

(54) LAYERED ELECTROOSMOTIC STRUCTURE

(71) Applicants: Osmotex AG, Thalwil (CH); Universitat Politecnica De Catalunya, Barcelona (ES); Institucio Catalana De Recerca I Estudis Avancats, Barcelona (ES)

(72) Inventors: Trond Heldal, Lucerne (CH); Andriy Yaroshchuk, Barcelona (ES)

(73) Assignees: OSMOTEX AG, Thalwil (CH); UNIVERSITAT POLITECNICA DE CATALUNYA, Barcelona (ES); INSTITUCIO CATALANA DE RECERCA I ESTUDIS AVANCATS, Barcelona (ES)

( * ) Notice: Subject to any disclaimer, the term of this patent is extended or adjusted under 35 U.S.C. 154(b) by 0 days.

(21) Appl. No.: 16/331,469

(22) PCT Filed: Sep. 8, 2017

(86) PCT No.: PCT/EP2017/072574
§ 371 (c)(1),
(2) Date: Mar. 7, 2019

(87) PCT Pub. No.: WO2018/046659
PCT Pub. Date: Mar. 15, 2018

(65) Prior Publication Data
US 2019/0255486 A1 Aug. 22, 2019

(30) Foreign Application Priority Data

Sep. 8, 2016 (ES) .................................. 201631175

(51) Int. Cl.
*B01D 61/46* (2006.01)
*A61M 1/00* (2006.01)
(Continued)

(52) U.S. Cl.
CPC ........... *B01D 61/46* (2013.01); *A61M 1/0072* (2014.02); *B01D 61/427* (2013.01); *B01D 69/02* (2013.01);
(Continued)

(58) Field of Classification Search
CPC ...... B01D 61/46; B01D 69/02; B01D 61/427; B01D 2325/42; F04B 43/043; F04B 19/006; A61M 1/0072
See application file for complete search history.

(56) References Cited

U.S. PATENT DOCUMENTS

| | | | |
|---|---|---|---|
| 2011/0308953 A1 | 12/2011 | Bazant et al. | |
| 2015/0283512 A1 | 10/2015 | Song et al. | |
| 2016/0252082 A1* | 9/2016 | Okumura | F04B 19/04 417/48 |

FOREIGN PATENT DOCUMENTS

| | | |
|---|---|---|
| JP | H05 220479 A | 8/1993 |
| WO | WO 2009/098486 A1 | 8/2009 |

(Continued)

OTHER PUBLICATIONS

International Search Report/Written Opinion of International Application No. PCT/EP2017/072574 dated Dec. 15, 2017 Sep. 29, 2017, 18 pages.

(Continued)

*Primary Examiner* — Arun S Phasge
(74) *Attorney, Agent, or Firm* — Fay Sharpe LLP

(57) ABSTRACT

A layered structure for pumping fluid by electroosmotic transport includes a first layer, wherein the first layer is made from an ion perm selective material having openings therein that permit the fluid to flow therethrough, and wherein the openings in the first layer that permit the fluid to flow therethrough create a porosity of less than 10%; and a second layer, wherein the second layer is an electroosmotic layer. The layered structure has a net fluid flow direction that (Continued)

extends through the first layer and the second layer, wherein the layered structure has a region that permits fluid to flow in a direction that is non-parallel to a net fluid flow direction, and wherein the region is located between the first layer and the surface of the second layer that is furthest from the first layer. An electroosmodialysis apparatus may also be provided that includes two layered structures.

19 Claims, 2 Drawing Sheets

(51) Int. Cl.
  *B01D 61/42* (2006.01)
  *B01D 69/02* (2006.01)
  *F04B 19/00* (2006.01)
  *F04B 43/04* (2006.01)

(52) U.S. Cl.
  CPC .......... *F04B 19/006* (2013.01); *F04B 43/043* (2013.01); *B01D 2325/42* (2013.01)

(56) References Cited

FOREIGN PATENT DOCUMENTS

| WO | WO 2012/022984 A1 | 2/2012 |
| WO | WO 2015/173359 A1 | 11/2015 |

OTHER PUBLICATIONS

United Kingdom Search Report of GB 1702542.0 dated Jul. 20, 2017, 4 pages.

\* cited by examiner

LAYERED ELECTROOSMOTIC STRUCTURE

BACKGROUND

The invention relates to a layered structure for pumping fluid by electroosmotic transport and a method of pumping a fluid through a layered structure by electroosmotic transport. The invention also concerns an electroosmodialysis apparatus that comprises the layered structure.

Structures for pumping fluid by electroosmotic transport, e.g. electroosmotic membranes, pumps and textiles, could be used in a wide range of applications for moisture and liquid flow control. Example application areas include microfluidic pumps, clothing (including leisure, sports, work and protective), medical (wound care, bed ulcer treatment etc), applications relating to climate control in automobiles, planes and buildings, etc. While electroosmosis can be driven by a DC current, the use of AC current has proven necessary, or at least provided a large improvement, in many applications due to the associated suppression of electrochemical reactions. This entails the complications that one needs an electroosmotic structure with current direction dependent transport properties, if the aim is to obtain a net transport of liquid in one direction. WO2015/173359 discloses some structures that have such direction dependent transport properties. However, there is a desire for alternative structures that have the potential to be less complex and easier to manufacture.

BRIEF SUMMARY

In a first aspect, the present invention provides a layered structure for pumping fluid by electroosmotic transport, the layered structure comprising: a first layer, wherein the first layer is made from an ion perm selective material having openings therein that permit the fluid to flow therethrough, and wherein the openings in the first layer that permit the fluid to flow therethrough create a porosity of less than 10%, or less than 5%; and a second layer, wherein the second layer is an electroosmotic layer, wherein the layered structure has a net fluid flow direction that extends through the first layer and the second layer, and wherein the layered structure has a region that permits fluid to flow in a direction that is non-parallel to a net fluid flow direction, wherein the region is located between the first layer and the surface of the second layer that is furthest from the first layer.

In a second aspect, the present invention provides a method of pumping a fluid through a layered structure by electroosmotic transport, the method comprising: providing a layered structure comprising: a first layer, wherein the first layer is made from an ion perm selective material having openings therein that permit the fluid to flow therethrough; and a second layer, wherein the second layer is an electroosmotic layer, wherein the layered structure has a net fluid flow direction that extends through the first layer and the second layer, and wherein the layered structure has a region that permits fluid to flow in a direction that is non-parallel to a net fluid flow direction, wherein the region is located between the first layer and the surface of the second layer that is furthest from the first layer; and applying an AC signal across the layered structure, wherein when a given amount of charge flows through the layered structure in a first direction more electroosmotic transport of the fluid occurs than when the same amount of charge flows through the layered structure in a second, opposite direction.

The present invention may have the advantage of reduced concentration dependence of EO flow, regardless of the use of AC or DC current. This reduced dependence, i.e. reduced sensitivity, may further improve the structure's stability/reliability. It may also introduce non-linear flow and beneficial conditions for electroosmosis, and hence an increase in flow and reduction in power for a given flow compared to conventional electroosmotic systems.

By the phrase the openings permit the fluid to flow therethrough used herein it may be meant that the openings permit the flow of fluid therethrough easily. This may mean that there is a reasonable flow of fluid through the openings rather than a small or negligible amount of fluid that may flow through an ion perm selective material in regions without the openings.

The openings in the first layer that permit the fluid to flow therethrough may create a porosity of less than 10%, or less than 5%, or less than 2%, or less than 1%. The porosity should be greater than 0%, i.e. there should be at least some openings.

The first layer may be referred to as an ion perm selective material layer.

The second layer may be referred to as an electroosmotic layer.

Thus the layered structure (i.e. electroosmotic structure) for pumping fluid by electroosmotic transport, may comprise: an ion perm selective material layer, wherein the ion perm selective material layer is made from an ion perm selective material having openings therein that permit the fluid to flow therethrough, and wherein the openings in the ion perm selective layer that permit the fluid to flow therethrough create a porosity of less than 10%, or less than 5% or less than 2%, or less than 1%; and an electroosmotic layer.

It is known that in electoosmotic materials, electroosmotic transport (which is dependent on the electrokinettic potential) is dependent on the electrolyte concentration. This is because the electrokinetic potential (zeta potential) for a charged surface is dependent on electrolyte concentration (e.g. the zeta potential may be lower at higher concentration). Specifically, the rate of electroosmotic transport is typically greater at low electrolyte concentrations.

It was realised that if a concentration polarisation could be induced in an electroosmotic layer in an asymmetric manner with regard to the voltage polarity applied across the layer that it may be possible to obtain directed electroosmotic flow with an AC current.

The present invention may provide a layered structure (i.e. a composite material) where the concentration polarization phenomena are largely "decoupled" from the porous medium but still influence the electroosmosis in the desired way. For example, the concentration polarisation effect may be induced by a layer other than the electroosmotic layer such that the electroosmotic layer may be optimised for electroosmotic transport whilst still being able to achieve directed fluid flow with a symmetric charge flow.

Ion perm selective materials experience current-induced concentration polarization close to their surface. Due to the very small pore size of such materials, these phenomena can occur up to quite high salinities. Moreover, at a given voltage drop the extent of concentration polarization is roughly independent of the salinity (for not too high salinities, i.e. below a threshold salinity). Therefore, it has been realised that if an electroosmotic layer (i.e. EO active porous medium) is provided next to, e.g. brought in close proximity to or direct contact with, an ion perm selective material layer, the electrolyte concentration at the interface and into the electroosmotic layer may be decreased or increased (depending on the current direction). This may occur even in solutions of rather high salinity.

Thus it has been realised that providing an ion perm selective material layer next to an electroosmotic layer could potentially make the electroosmotic transport strongly non-linear and asymmetric with respect to the voltage.

However the hydraulic permeability of conventional ion perm selective material layers is extremely low. Therefore, when a layer made of ion perm selective material is brought next to an electroosmotic layer, the electroosmotic layer may cause a large gradient of hydrostatic pressure between the two layers but, due to the low hydraulic permeability of the ion perm selective material layer, the volume flow through the layered structure may be very low.

It has been realised that an effective electroosmotic structure could be created if the hydraulic permeability of the ion perm selective material layer can be increased whilst maintaining the ability of the ion perm selective material layer to induce a concentration polarisation in the electroosmotic layer.

In the present invention this is achieved by having openings in the ion perm selective material layer that permit the fluid to flow therethrough. These openings may create a porosity of less than 10%, less than 5%, less than 2%, about 1%, 0.1 to 2% or 0.1 to 1% in the ion perm selective material layer. By porosity it may be meant the perforated fraction of the surface area, e.g. a layer with 5% porosity may have 5% of its surface area as openings The openings in the first layer may be distributed evenly, or relatively evenly, over its surface. The openings may be randomly distributed and/or selectively positioned at equal distances. However, the openings may not to a large degree be clustered. This is to ensure that the bulk flow of fluid and the zones of concentration polarization are relatively evenly distributed over the surface of the first layer.

Thus by having relatively scarce microscopic pores/channels in the ion perm selective material layer it is possible to increase the hydraulic permeability of the ion perm selective material layer whilst still allowing it to induce a concentration polarisation in the electroosmotic layer.

Hydraulic permeability is a strong function of pore size. Therefore, even a relatively small fraction (a fraction, a few or a couple of percent) of microscopic openings (e.g. pores/channels) can make the hydraulic permeability of ion perm selective material layer orders of magnitude larger.

The layered structure may be arranged so that the hydraulic permeability of the ion perm selective material layer is higher, e.g. much higher, than the hydraulic permeability of the electroosmotic layer.

In this case, the rate of electroosmotic fluid transport may be controlled by the processes in the electroosmotic layer and may be hydraulically unaffected by the presence of ion perm selective material layer with openings therein.

At the same time, the process of current-induced concentration polarization may be less influenced by the openings because the effect of the openings on this effect is roughly proportional to their surface fraction, which may be quite small (due to the low porosity).

According to the Hagen-Poiseuille equation, the hydraulic permeability of a porous medium is proportional to its porosity and the square of pore size.

As an example, assuming the same thickness for the EO-active medium and the porous ion perm selective material layer, a pore size of 100 nm and a porosity of 40% in the electroosmotic layer, and a pore size of 2 µm and a porosity of 1% in the ion perm selective material layer, the hydraulic resistance of the latter will be about 1 order of magnitude lower than that of the electroosmotic layer.

Therefore, in the present invention, the electroosmotic layer may be able to effect liquid transport (i.e. electroosmotic transport) through the layered structure as if the ion perm selective material layer did not exit.

Continuing the example given above (a pore size of 100 nm and a porosity of 40% in the electroosmotic layer, and a pore size of 2 µm and a porosity of 1% in the ion perm selective material layer), the average distance between the openings in the ion perm selective material layer will be about 20 µm. This distance is noticeably smaller than the typical thickness (which may for example be about hundred microns) of electroosmotic layer. Due to this, the concentration within the electroosmotic layer may be approximately constant within a major part of its thickness.

The average distance (e.g. the centre of an opening to the centre of an adjacent opening distance or edge of an opening to the edge of an adjacent opening distance, both of which are approximately the same due to the fact that the size of the openings is much smaller than the space between them) between the openings may be equal to or less than the thickness of the electroosmotic layer. The distance between the openings may be noticeably less than the thickness of the electroosmotic layer.

The distance between the openings may be between 0.01 to 0.95, 0.1 to 0.75 or about 0.5 of the thickness of the electroosmotic layer.

The size (e.g. diameter) of the openings may be significantly less than the thickness of the electroosmotic layer.

The electroosmotic layer may be between 10 to 100 microns thick, for example, between 20 and 80 microns thick or about 50 microns thick.

The ion perm selective layer may be as thin as possible. This may for example be as thin as can be feasibly and/or reliably manufactured.

The ion perm selective layer may be sufficiently thin such that the thickness does not affect the hydraulic permeability of the structure to any significant extent. The hydraulic permeability of the ion perm selective layer will depend on the width of the openings and the distance between the openings.

The ion perm selective layer may have a thickness between 1 and 100 microns, or between 3 and 30 microns.

Because of this, at one current direction, a major part of the electroosmotic layer may be filled with solution of lower electrolyte concentration occurring due to the concentration polarization at the surface of the largely non-porous matrix of the ion perm selective material layer. Accordingly, the rate of electroosmotic transport will be high in the case of this current direction. At the opposite current direction, the electrolyte concentration within the electroosmotic layer may be increased (albeit to an essentially smaller extent than decreased in the previous case) and the rate of electroosmotic may be lower at the same current magnitude.

Bulk fluid may flow through the openings in the ion perm selective material layer whilst the concentration polarization effect can still occur at the surface of the ion perm selective material except the openings (as there is no ion perm selective material at the openings).

The present invention may provide a layered structure in which when a given amount of charge flows through the layered structure in a first direction more electroosmotic transport of the fluid will occur than when the same amount of charge flows through the layered structure in an opposite second direction.

The present invention may provide a layered structure in which when a voltage is applied across the structure a greater concentration polarisation will be induced in the electroosmotic membrane than when an opposite voltage of equal magnitude is applied across the structure.

The present invention may provide a layered structure in which when a voltage is applied across the structure a concentration depletion (and hence a higher rate of electroosmotic transport) will be induced and when an opposite voltage is applied across the structure a concentration enrichment (and hence a lower rate of electroosmotic transport) will be induced.

In the present invention the asymmetric electroosmotic effect may be effective (i.e. work) over a broad range of ionic concentrations.

This is because, due to the very small pore size of ion perm selective materials, current induced concentration polarisation can occur up to quite high salinities. Moreover, at a given voltage drop the extent of concentration polarization induced is roughly independent of the salinity (for not too high salinities, i.e. below a threshold salinity).

This may increase the reliability of the system, especially in uses where concentration cannot be controlled. Even in cases where the fluid and its concentration can be selected, its local value in the concentration polarization zone will vary and can be difficult to know with reasonable accuracy.

The layered structure may have a reasonable pore size to allow a reasonable magnitude of electroosmotic and current flow through the system.

For example, for a current of 1 to 10 Ampere per square meter, the rate of electroosmotic transport may range from 1 up to 100 litre/m$^2$/hour.

The electroosmotic membrane may have porosities in the range 1 to 80%, and pore size from 50 up to 300 nm.

The electroosmotic membrane may have a porosity that is greater than the porosity of the ion perm selective material layer.

The electroosmotic membrane may have a pore size that is smaller than the openings in the ion perm selective material layer.

The layered structure may also be referred to as an electroosmotic structure, device or membrane. The structure may for example be, or be part of, an electroosmotic pump and/or an electroosmotic textile.

The layered structure may be regarded as a composite material/membrane.

In use, the layered structure may be filled with and/or be immersed in an ionic aqueous solution.

The electroosmotic layer may be a layer which effects electroosmotic transfer of fluid therethrough when a voltage is applied across the layer.

The electroosmotic layer may be a porous medium, e.g. a porous membrane.

The pores of the electroosmotic layer may have a width dimension that is approximately equal through the thickness of the layer. For example, the average pore size may be substantially constant in the electroosmotic layer.

The electroosmotic layer may for example be a track-etched membrane, or a membrane produced by phase inversion like nanoporous membranes from the companies Millipore or Pall (i.e. nanoporous grades of Millipore/Pall membrane).

The ion perm selective material may be referred to as a perm selective ion conductive material. The ion perm selective material may be an ion exchange material. The perm selective material may be a material that has significantly higher conductivity and diffusivity of ions of one sign. For example, significantly higher may mean that the conductivity and diffusivity of ions of one sign is at least two times, or at least 10 times the conductivity and diffusivity of ions of the opposite sign.

Example ion perm selective materials which may be used include aminated (anion exchange) or sulfonated (cation exchange) polystyrene which is crosslinked with divinyl benzene. Another example is fluorinated polymers which carry sulfonic acid groups, like DuPont's Nafion® membrane.

The electroosmotic layer may be made for example from aminated or sulfonated PET or PES membranes. The groups of the ion perm selective material and/or the electroosmotic layer may be selected so that the layers have opposite fixed charges.

The ion perm selective material layer (i.e. the first layer) and the electroosmotic layer (i.e. the second layer) may be in close proximity to each other.

The ion perm selective material layer and the electroosmotic layer may be located such that a concentration polarisation effect induced at the surface of the ion perm selective layer in use extends at least partially into the electroosmotic layer.

For example, the surfaces of the ion perm selective material layer (i.e. the first layer) and the electroosmotic layer (i.e. the second layer) closest to each other may be a distance of less than 500 µm, less than 100 µm, less than 10 µm, less than 5 µm or less than 1 µm from each other.

The ion perm selective material layer (i.e. the first layer) and the electroosmotic layer (i.e. the second layer) may be in direct contact.

The first and second layers may be fixed to each other. For example, the two layers may be bonded and/or laminated together. The two layers may be held together mechanically. The layered structure may consist of the two layers.

A third layer may be provided between the first and second layers as discussed in more detail below. In the case that a third layer is provided the layered structure may consist of the three layers.

The openings in the ion perm selective material layer may be pores, channels, holes and/or cracks etc.

The openings may be microscopic openings. This may mean that the openings have a height and/or width dimension (i.e. dimension in the plane of the layer rather than length that is the dimension in a through direction of the layer) that is of the order of microns. The openings may be 0.1 to 10 µm, 0.5 to 3 µm, 0.5 to 2 µm, 0.5 to 1.5 µm or about 1 µm.

The electroosmotic layer may have openings/pores therein that have an average pore size of 10 to 500 nm, 50 to 150 nm or about 100 nm.

The electroosmotic layer may be a porous membrane (e.g. a layer with a foamy structure). The electroosmotic layer may be a perforated layer, e.g. a track etched membrane.

Due to the low porosity the openings in the first layer may be relatively scarce. The openings may be below 10%, or below 5%, or below 2%, or below 1% of the surface of the first layer (e.g. the surface percentage of openings in the ion perm selective material layer may be the same as the porosity).

The first layer may be perforated. The ion perm selective material layer may be formed from an ion perm selective material in which openings have been formed or from an ion perm selective material that already has openings therein.

The openings may be 'defects' in the ion perm selective material layer, i.e. non-ordered and/or non-regular openings. These defects may have been introduced in a controlled manner, i.e. deliberately introduced and/or have parameters such as porosity and pore size that is controllable.

The 'defects', i.e. openings, for example may be cracks in the ion perm selective material layer.

The ion perm selective material layer may be formed by sintering and the openings may be the gaps between the parts of the particles that are not fully sintered together. These could be regarded as 'defects'. However, such 'defects' may be controllable in that the level of porosity and/or average pore size may be controlled by adjusting the sintering time and/or temperature.

The first layer may be a porous membrane made from an ion perm selective material, e.g. a perforated film made of an ion perm selective material.

The layered structure has a net fluid flow direction that extends through the first layer and the second layer and the second layer may be on the downstream side of the first layer. In other words, net electroosmotic transport may be obtained in the direction from the ion perm selective material layer towards the electroosmotic layer.

The direction that current needs to flow to cause net fluid flow depends on the fixed surface charge of the electroosmotic membrane and the fixed charge of the ion perm selective membrane.

In the case in which the electroosmotic layer has pores with a negative surface charge (such as those with sulfonic acid groups), the perm selective layer may selectively transport negative ions. This may result in a lowering of electrolyte concentration in the electroosmotic layer and hence higher electroosmotic transport when a positive current passes from the perm selective layer towards the electroosmotic layer.

In the case in which the electroosmotic layer has pores with a positive surface charge, the perm selective layer may selectively transport positive ions. This may result in a lowering of electrolyte concentration in the electroosmotic layer and hence higher electroosmotic transport when a positive current passes from the electroosmotic layer towards the perm selective layer.

The layered structure has a region (which may be referred to as a mixing region or mixing layer) that permits fluid to flow in a direction that is non-parallel to a net fluid flow direction. The mixing region may be located between the first layer and the surface of the second layer that is furthest from the first layer (i.e. the outer edge of the first layer). In other words, the region may be between the surface of the first layer that is closest the second layer and the surface of the second layer that is furthest from the first layer. This means that the mixing region may be provided by the second layer itself and/or provided by an additional layer between the first and second layers.

The region may permit fluid to flow in a direction that is non-parallel to the direction that fluid flows through the openings of the ion perm selective material layer.

The mixing region may have pores that extend in a lateral, or partially lateral direction, as well as in the through, or partially through (normal to the surface of the layered structure) direction.

The lateral and through pores may be interconnected, i.e. the region may have interconnected porosity in both directions. The region may have a random and/or foamy/spongy type of structure.

The region that permits fluid to flow in a direction that is non-parallel to the net fluid flow direction may comprise pores that extend in a direction that is non-parallel to the net fluid flow direction.

The mixing region may be beneficial because of the varying effects on the surface of the ion perm selective material layer. As discussed above, at the points where the openings are provided bulk fluid flow may occur through the ion perm selective material layer and at the surface between the openings (where there is no bulk fluid flow) concentration polarisation may be induced. This may result in zones at the surface of the ion perm selective material layer having concentration polarisation but no fluid flow and zones having fluid flow but no concentration polarisation. The mixing region may allow the effects of these two zones to mix such that fluid flow can occur in regions of concentration polarisation.

The mixing region may allow the liquid flowing through the pores of the ion perm selective material layer to mix with the lower concentration liquid created by concentration polarisation at the parts of the ion perm selective material layer that are not openings.

The mixing region may be, or may be part of, the electroosmotic layer, i.e. the second layer may comprise, or be, the region that permits fluid to flow in a direction that is non-parallel to the net fluid flow direction.

The mixing region may be provided by pores in the electroosmotic layer that are non-parallel to the fluid flow direction. These non-parallel pores may be provided across the full width of the electroosmotic layer or may be provided in just part of the electroosmotic layer, such as in a region that is closest to the ion perm selective material layer.

The region that permits fluid to flow in a direction that is non-parallel to the net fluid flow direction may be provided additionally or alternatively by a third layer located between the first layer and the second layer. The third layer may be referred to as a mixing layer.

This third layer may be a membrane with a fibrous structure (made e.g. by electrospinning) or a foamy structure (made e.g. by phase inversion).

The third layer may have no surface charge, a low surface charge or a surface charge of same sign as the electroosmotic layer. The third layer may also be a binder or glue layer, e.g. a thermoplastic web glue.

A third layer may for example be provided when the electroosmotic layer is a track etched membrane.

When a third layer is provided, the first layer and/or the second layer may be in direct contact or close proximity with the third layer. The first and/or second layer may be fixed to the third layer. For example, the three layers may be bonded and/or laminated together. The three layers may be held together mechanically.

Even when a third layer is interposed between the first and second layers, the surfaces of the ion perm selective material layer (i.e. the first layer) and the electroosmotic layer (i.e. the second layer) closest to each other may be a distance of less than 500 µm, less than 100 µm, less than 50 µm or less than 10 µm from each other. The third layer may have a thickness of less than 500 µm, less than 100 µm or less than 50 µm or less than 10 µm.

The region that permits fluid to flow in a direction that is non-parallel to the net fluid flow direction (whether that is as part of the electroosmotic layer or a separate mixing layer) may have a thickness that is at least 2 times, or at least 4 times the average distance between the openings of the first layer.

The electroosmotic layer may have a fixed surface charge. This fixed surface charge may be of the same sign as the sign of the ions to which the material of the first layer is perm selective. Thus, the fixed surface charge of the electroosmotic layer may be the same sign as the charge of the predominant current carrier in the layered structure.

The sign of the ions to which the material of the first layer is perm selective may be opposite to the sign of the fixed charge of the material of the first layer.

The fixed surface of the electroosmotic layer charge may be the opposite sign of the fixed charge of the material of the first layer.

The ion perm selective material may be of an opposite charge to the charge of the electroosmotic membrane.

The ion perm selective material layer may be an anion exchange membrane. The ion perm selective material layer may have fixed quaternary amine groups. The electroosmotic membrane may have sulfonic acid groups that create the fixed pore wall charge.

The ion perm selective material layer may have fixed sulfonic acid groups. The electroosmotic membrane may have quaternary amine groups that create the fixed pore wall charge.

The ion perm selective material layer may result in concentration polarisation and hence reduced concentration inside the electroosmotic layer when an electric current carried by the electroosmotic layer's surface charge's counter ions is being passed in the direction from the perm selective material layer towards the electroosmotic layer.

Counter ions are mobile ions of opposite charge to the fixed ions, e.g. on the electroosmotic layer surface or in the ion perm selective material.

The ion perm selective material layer and/or the electroosmotic layer may be polymer membranes.

An ion perm selective material may be provided on only one side of the electroosmotic layer. This may ensure that the induced concentration polarisation in the electroosmotic layer is asymmetric.

The layered structure may be arranged so that, when electric current is passed through the layered structure in a first direction, the electrolyte concentration in the second layer will be decreased and, when electric current is passed through the layered structure in a second direction opposite to the first direction, the electrolyte concentration in the second layer will be increased.

The layered structure may be arranged so that, when electric current is passed through the layered structure in a first direction, a first concentration polarisation (depletion) is induced in the second layer and, when electric current is passed through the layered structure in a second direction opposite to the first direction, a second opposite (enrichment), concentration polarisation is induced in the second layer.

The first electric current direction may correspond to the movement of ions, for which the material of the first layer is perm selective, away from the second layer and towards the first layer.

The layered structure may be arranged so that when a given amount of charge flows in the first direction more electroosmotic transport of the fluid will occur through the layered structure than when the same amount of charge flows in the second direction.

The layered structure may be arranged so that net fluid flow can be achieved when an AC voltage is applied across the layered structure.

The layered structure may comprise, or be located between, two electrodes. One electrode may be at or near the surface of the ion perm selective material layer (the surface furthest from the electroosmotic layer) and the other electrode may be at, or near, the surface of the electroosmotic layer (the surface furthest from the ion perm selective material layer).

The system may comprise a first electrode and a second electrode, wherein the first electrode is provided on one side of the layered structure and the other electrode is provided on the opposite side of the layered structure. The electrodes may be arranged so that a voltage can be provided across the layered structure. The electrodes may be porous so that fluid transported through the porous layered structure can pass through the electrodes. The pore size of the electrodes may be greater than the pore size of the layered structure so that they do not provide a significant resistance to the flow of fluid through the layered structure.

The electrodes may be textiles. The electrodes may be capacitive or redox couple electrodes. The electrodes may be capacitive ("activated") carbon electrodes.

The electrodes may be reversible or polarizable electrodes.

The electrodes may be coated onto the layered structure, such as by chemical or physical vapor deposition techniques. Alternatively, the electrodes may be made of separate layers, like a textile, carbon cloth or non-woven material coated with metal or a redox couple. The electrodes may be held or located at certain distances from the layered structure.

The electrodes may be in direct contact with, or in close proximity to, i.e. within 10 nm or within 100 nm, of the first and second opposite surfaces of the layered structure.

The layered structure may form at least part of an electroosmotic fabric. The fabric may comprise porous capacitive electrodes on each side.

A voltage may be applied across the layered structure using the electrodes.

The applied signal may be a voltage controlled AC signal, or a current controlled AC signal.

Examples of a voltage controlled signal may be a square pulse signal with a potential of +1 V for 10 seconds followed by −1 V for 10 seconds. An example current controlled AC signal may be a square pulse signal with current 100 mA (milliampere) for 10 seconds, followed by a pulse of 100 mA for 10 seconds. The frequency of the signal may be lower than the time needed for the concentration polarization to develop, typically between 1 and 20 seconds and/or an electric signal and charge controlled as disclosed in WO2012/022984.

The structure may be arranged so that it can be operated using low frequency AC voltage. The voltage may be below the electrolysis voltage of the liquid to be pumped (which for example is 1.2V for water).

The electric signal applied across the structure to effect fluid flow may be AC or pulsed DC. It may be in the form of current pulses, for example symmetric square pulses.

The signal may be such that over a period of time (e.g. a second or a minute for example) there is no net flow of charge across the layered structure.

The method may be such that, in a given amount of time, there is no (or not substantial) net flow of charge across the layered structure.

By zero or no net charge flow it is meant that the same amount of charge is passed through the layered structure (e.g. between electrodes which may be on opposite sides/surfaces of the layered structure) in both directions when averaged over several pulses or reversals of the voltage bias. The magnitude, duration and current of the opposite pulses applied across the membrane may be different. However, the signal may be controlled such that the net flow of charge over a given amount of time is zero, or near zero.

The electrical signal applied across the layered structure may be arranged to cause no, or only a small, net charge flow over time in order to operate the electrodes reversibly or near reversibly. In the case there is no net charge flow over time, the period of time over which no net charge is passed may be of the order of milliseconds, seconds, minutes, hours or even days or more depending on the electrical signal applied across the membrane.

A system comprising the layered structure may be operated in a potentiostatic mode (voltage controlled) and/or galvanostatic mode. Alternatively, it may be operated in a "charge counting" mode, with the voltage (magnitude or bias) or length of pulses being automatically adjusted to assure equal charge transfer in both directions.

In the present invention a net electroosmotic transport of fluid may be achieved in the net fluid flow direction even when the same amount of charge passes back and forth though the layered structure, i.e. when there is no net flow of charge.

The present invention provides a layered structure in which, for a given amount of charge flowing through the structure in one direction (from the first surface to the opposite second surface of the structure, i.e. in the structure thickness direction), more electroosmotic transport will be induced than when the same amount of charge flows through the layered structure in the opposite direction. This has the advantage that the layered structure can be used with an alternating current whilst still obtaining net electroosmotic flow.

In a preferred embodiment, the present invention provides a layered electroosmotic structure for pumping fluid by electroosmotic transport, the layered structure comprising: a first layer, wherein the first layer is made from an ion perm selective material having openings therein that permit the fluid to flow therethrough, and wherein the openings in the first layer that permit the fluid to flow therethrough have a width dimension of 0.1 to 10 µm and create a porosity of less than 5%, or less than 2% or less than 1%; and a second layer, wherein the second layer is an electroosmotic layer, and wherein the structure comprises a region that permits fluid to flow in a direction that is non-parallel to the direction in which fluid, in use, flows through the openings of the first layer.

The layered structure may be used in clothing, sports equipment, vehicle and building interior materials to provide a means of effective directed fluid transport. The layered structure may alternatively be used as a medical textile, e.g. for bed sore prevention or treatment, wound treatment etc. The structure may be used to remove condensation or other moisture in electronic, mechanical and medical devices. The structure may be used as an actuator in a mechanical or fluidic system. This is a list of exemplary applications but is by no means exhaustive.

The present invention may provide an electroosmotic pump for pumping a fluid by electroosmotic transport, the pump comprising a passageway forming a flow path for fluid transport, a layered structure located across the passageway, the layered structure comprising: a first layer, wherein the first layer is made from an ion perm selective material having openings therein that permit the fluid to flow (e.g. easily) therethrough, and wherein the openings in the first layer that permit the fluid to flow therethrough create a porosity of less than 10%, or less than 5%, or less than 2% or less than 1% (but greater than 0%); and a second layer, wherein the second layer is an electroosmotic layer.

The present invention also provides an electroosmotic pump comprising the layered structure of the first aspect (including one or more of the above described optional features).

The pump may be a micropump.

The present invention may provide an electroosmotic textile, the textile comprising a layered structure for pumping fluid by electroosmotic transport, the layered structure comprising: a first layer, wherein the first layer is made from an ion perm selective material having openings therein that permit the fluid to flow (e.g. easily) therethrough, and wherein the openings in the first layer that permit the fluid to flow therethrough create a porosity of less than 10%, or less than 5% or less than 2% or less than 1% (but greater than 0%); and a second layer, wherein the second layer is an electroosmotic layer.

The present invention also provides an electroosmotic textile comprising the layered structure of the first aspect (including one or more of the above described optional features).

The electroosmotic textile may also comprise a fabric layer(s) and/or may be a textile product.

The fabric layer(s) is (are) preferably made of woven material. An example of a textile product is a waterproof jacket, which may incorporate an electroosmotic layered structure as described herein for the removal of perspiration away from the body.

The system (e.g. pump or textile) may comprise a power source. The power source may be arranged to apply a voltage across the layered structure. The power supply may provide AC or DC voltage. When the power supply provides DC voltage, the system may be arranged to reverse the polarity of the DC voltage periodically, for example, on the order of seconds, minutes, or hours.

The magnitude of the voltage in opposite pulses may be different. However, in this case, the length of time of the pulses may be controlled so that over a given period of time (which may be over a number of pulses) there is zero, or only a small, net charge transfer. In other words, the current between opposite pulses may vary providing that, in use, there is no, or only a small, net charge flow over a certain period of time and a certain number of pulses.

In the case of zero net charge flow, there does not necessarily need to be zero net charge transfer between consecutive pulses, providing the average net charge transfer over a number of pulses (such as 3 or more) is zero.

In the case of zero net charge flow, the given amount of time over which there is no net flow of current may be of the order of seconds, minutes or hours depending on the electrical signal applied.

The electrical signal which causes the charge flow across the layered structure may be an AC voltage or a pulsed DC voltage.

The present invention may comprise a method of effecting electroosmotic transport using the layered structure of the first aspect (including one or more of the above described optional features).

The method may be such that, in a given amount of time, there is no, or only a small, net flow of charge across the membrane.

In its broadest aspect, the present invention provides a layered structure for pumping fluid by electroosmotic transport, the layered structure comprising: a first layer, wherein the first layer is made from an ion perm selective material; and a second layer, wherein the second layer is an electroosmotic layer.

The layered structure may have one or more of the above described features including the optional features.

It has been realised that two layered structures that each comprises an ion perm selective material layer and an electroosmotic layer can be used to create an electrodialysis device.

The electrodialysis device may be referred to as an electroosmodialysis device. This is because it is a device that may cause electrodialysis due to the selective movement of ions through the first layer and the movement of volume by electroosmosis that is due to an electric field applied across the layers.

In a third aspect, the present invention provides an electroosmodialysis apparatus, the apparatus comprising: a first layered structure comprising a first layer, wherein the first layer is made from an ion perm selective material having openings therein that permit the fluid to flow (e.g. easily) therethrough; and a second layer, wherein the second layer is an electroosmotic layer; and a second layered structure comprising a third layer, wherein the third layer is made from an ion perm selective material having openings therein that permit the fluid to flow (e.g. easily) therethrough; and a fourth layer, wherein the fourth layer is an electroosmotic layer; and a volume between the first and second layered structures into which fluid is transported when a current is passed through the first and second layered structures.

In a fourth aspect the present invention provides a method of performing electroosmodialysis, the method comprising: providing an electroosmodialysis apparatus, the apparatus comprising: a first layered structure comprising a first layer, wherein the first layer is made from an ion perm selective material having openings therein that permit the fluid to flow (e.g. easily) therethrough; and a second layer, wherein the second layer is an electroosmotic layer; and a second layered structure comprising a third layer, wherein the third layer is made from an ion perm selective material having openings therein that permit the fluid to flow (e.g. easily) therethrough; and a fourth layer, wherein the fourth layer is an electroosmotic layer; and a flow path between the first and second layered structures into which fluid is transported when a current is passed through the first and second layered structures, and passing a current through the first and second layered structures to cause electroosmodialysis.

The electroosmodialysis apparatus may be the electroosmodialysis apparatus of the third aspect and optionally may include one or more of the following optional features.

The volume between the first and second layered structures may be referred to as a flow path. The volume may be a channel, e.g. narrow channel, separating the first and second layered structures. The volume may be created by a spacer between the first and second layered structures.

The apparatus may be arranged so that when the device is immersed in a liquid environment and a current is passed through the first and second layered structures, fluid transported into the volume from the liquid environment is of a lower electrolyte concentration than fluid of the liquid environment that has not been transported into the volume.

The volume may be isolated from the liquid environment such that fluid will not flow from the liquid environment in to the volume other than through the layered structures.

The ion perm selective material of the first layer of the first layered structure and the ion perm selective material of the third layer of the second layered structure may be of opposite polarity, i.e. have opposite fixed charges.

For example, the first layer may be made of an anion exchange material and the third layer may be made of a cation exchange material, or vice versa.

The second layer (electroosmotic layer of the first layered structure) may have a surface charge that is of a sign opposite to the fixed charge of the first layer (ion perm selective material layer of the first layered structure) and/or the fourth layer (electroosmotic layer of the second layered structure) may have a surface charge that is of a sign opposite to the fixed charge of the third layer (ion perm selective material layer of the second layered structure).

The second and fourth layers may have surface charges of the same sign as the charge to which the ion perm selective material of the respective attached layer is perm selective.

The two layered structures on either side of the volume may be regarded as "mirror image" structures.

The first layered structure and/or the second layered structure may be the layered structure of the first aspect. One or both of the layered structures may have any one or more of the features of above described layered structure including one or more of the optional features.

In the present invention, bulk liquid is transported through the layered structures. At a given current direction, liquid of reduced salinity will be pumped electro-osmotically into the volume between the two layered structures.

The present invention may not experience a limiting current. This is because when a current flows through the structure in a certain direction concentration polarisation is induced in the electroosmotic membranes that can increase the rate of electroosmotic flow. This means that the invention may provide a device for deionising water at a higher rate for a given voltage and hence smaller membrane areas and lower costs compared to conventional electrodialysis apparatuses.

The openings in the first and/or third layers that permit the fluid to flow therethrough may have a width dimension of 0.1 to 10 μm. Additionally or alternatively, the openings may create a porosity of less than 10%, less than 5%, less than 3%, about 1%, 0.1 to 2% or 0.1 to 1%.

One or both of the layered structures may comprise a region that permits fluid to flow in a direction that is non-parallel to the direction in which fluid, in use, flows through the openings of the respective first and/or third layer.

BRIEF DESCRIPTION OF THE DRAWINGS

Certain preferred embodiments of the present invention will now be described by way of example only with reference to the accompanying drawings, in which.

DETAILED DESCRIPTION

Figure 1:
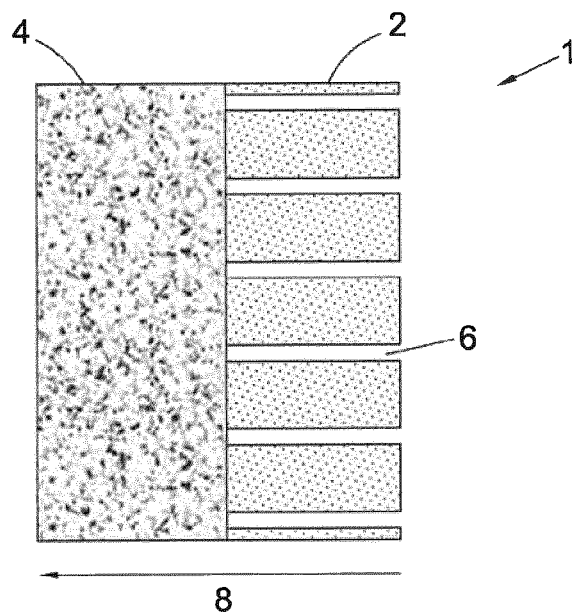
FIG. 1 is a schematic of an exemplary layered structure.

FIG. 1 shows an electroosmotic layered structure 1. The structure 1 comprises a first layer that is an ion perm selective material layer 2 and a second layer that is an electroosmotic layer 4.

The ion perm selective material layer 2 is a layer made from an ion perm selective material. The perm selective material is a material that has significantly higher conductivity and diffusivity of ions of one sign. For example, the conductivity and diffusivity of ions of one sign is at least two times, or at least 10 times the conductivity and diffusivity of ions of the opposite sign.

The ion perm selective material has microscopic pores 6 therethrough that permit fluid to flow through the layered structure. The fact that the pores 6 are microscopic pores may mean that they have a width (dimension in a direction parallel to the surface of the structure 1 and perpendicular to the direction in which fluid flows through the structure 1) between 0.1 and 10 microns.

The electroosmotic layer 4 is a layer that has a fixed surface charge and will cause transport of liquid by electroosmotic flow when a voltage is applied across the layer 4.

When a voltage is applied across the layered structure 1 fluid will flow in a net direction from the ion perm selective material layer 2 to the electroosmotic layer 4 as illustrated by arrow 8.

The electroosmotic layer 2 may have a structure that permits fluid to flow in a direction that is parallel to the net fluid flow direction 8 and to flow in a direction (i.e. a lateral direction) that is non-parallel to the net fluid flow direction 8.

Figure 2:
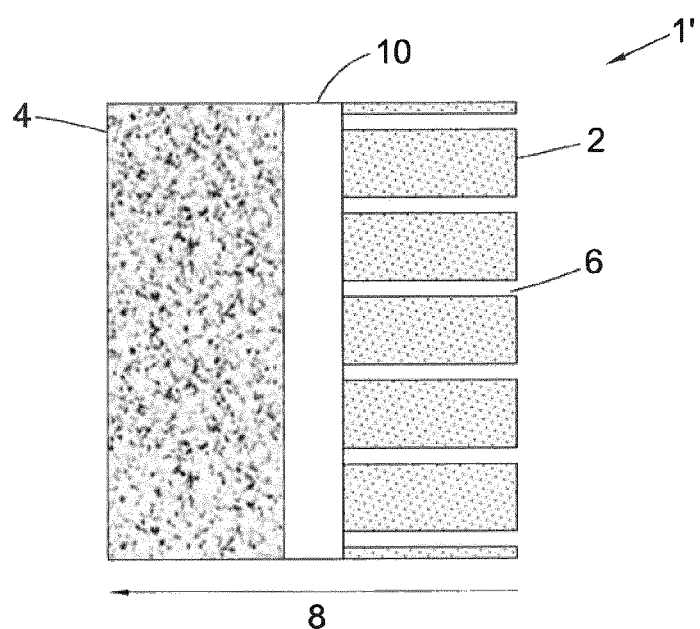
FIG. 2 is a schematic of another exemplary layered structure.

As shown in FIG. 2, the layered structure 1' may comprise a third layer, a mixing layer 10 between the ion perm selective material layer 2 and an electroosmotic layer 4. The mixing layer 10 may be a porous structure that permits fluid to flow in a lateral direction (i.e. a direction that is non-parallel to the net fluid flow direction 8). This may be particularly beneficial when the electroosmotic layer 4 only has pores that permit fluid flow in a direction substantially parallel to the net fluid flow direction.

The ion perm selective material layer 2 and the electroosmotic layer 4 may have opposite fixed charges. The fixed surface charge of the electroosmotic membrane 4 may be the same sign as the sign of the ions for which the ion perm selective material is perm selective. For example, the electroosmotic membrane 4 may have a negative fixed surface charge and the material of the ion perm selective material layer 2 may have higher conductivity and diffusivity of anions or the electroosmotic membrane 4 may have a positive fixed surface charge and the material of the ion perm selective material layer 2 may have higher conductivity and diffusivity of cations.

The structure 1, 1' may be provided on either side with an electrode that permits a voltage to be applied across the structure 1, 1', i.e. structure 1, 1' may be located between two electrodes.

When a voltage of a first polarity is applied across the layered structure 1, 1', a current flows through the structure 1 in a first direction. A given current flow direction (the direction being dependent on the sign of the ion to which the ion perm selective material layer 2 is permselective) induces a concentration polarisation at the surface of the ion perm-selective material layer 2 that extends into the electroosmotic layer 4.

This concentration polarisation reduces the electrolyte concentration in the electroosmotic layer 4 and that increases the rate of electroosmotic transport.

When a voltage of a second opposite polarity is applied across the layered structure 1, 1', a current flows through the structure 1 in a second opposite direction. This increases the electrolyte concentration in the electroosmotic layer 4 and that decreases the rate of electroosmotic transport. This allows the structure 1, 1' to have a net electroosmotic transport through the structure 1, 1' even when there is no net charge flow (i.e. over a period of time the same amount of charge will flow in each opposite direction) such as when an AC signal is used.

Figure 3:
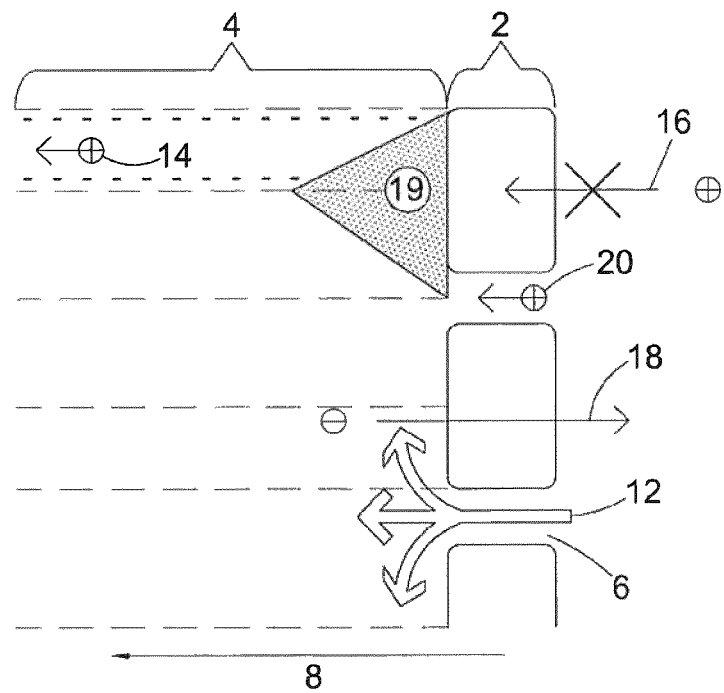
FIG. 3 is a schematic to help illustrate how the layered structure works.

FIG. 3 illustrates schematically the effect of the two structures together.

This shows the ion perm selective material layer 2 with openings 6 therein that permit bulk fluid flow through. The electroosmotic layer 4 has openings in the structure that allow fluid to flow in a direction that is non-parallel to the net fluid flow direction 8. As illustrated by multi headed arrow 12, fluid can flow through the ion perm selective material layer 4 and into the electroosmotic layer 4 where it can flow in directions non-parallel to the net fluid flow direction so as to permit mixing of the fluid flowing through the openings 6 with the fluid at or near the surface of the ion perm selective material layer 2 where there are no openings.

As shown in the upper most pore of the electroosmotic layer 4, there are negative surface charges of the pores of the electroosmotic layer 4. This results in movement of positive movable ions (illustrated schematically at 14) near the surface of the electroosmotic layer pores to compensate the negative charge (the fixed surface charge and the movable ions together form an electric double layer). The positive ions move in response to the electric field imposed by electrodes (not shown) and results in electroosmosis.

As shown schematically at arrow 16, the positive ions are blocked by the perm selective material whilst, as shown at arrow 18, the negative ions can pass through the perm selective material. As shown at 20, ions of both sign can pass through the openings in the perm selective material.

The perm selectivity of layer 2 and the restrictions to mixing with bulk liquid (as the lateral pores do not allow complete mixing) caused by the electroosmotic membrane 4 results in the formation of a concentration polarization zone 19. This zone 19 extends into the thickness of the electroosmotic layer 4. The triangle shape of this zone 19 is purely schematic and just indicates the direction in which the zone will grow (and not the real shape of the zone). Depending on the electroosmotic layer 4, the depleted zone 19 might reach part of or the whole of its thickness at steady conditions.

The concentration polarisation 19 reduces the electrolyte concentration in the electroosmotic layer 4. This results in an increased rate of electroosmosis.

When a voltage of opposite polarity is applied across the structure 1, 1', a charge will flow in an opposite direction. This will increase the electrolyte concentration in the electroosmotic layer 4. This results in a decreased rate of electroosmosis. Thus, the structure 1, 1' may have an asymmetric (and therefore net) electroosmotic flow.

Figure 4:
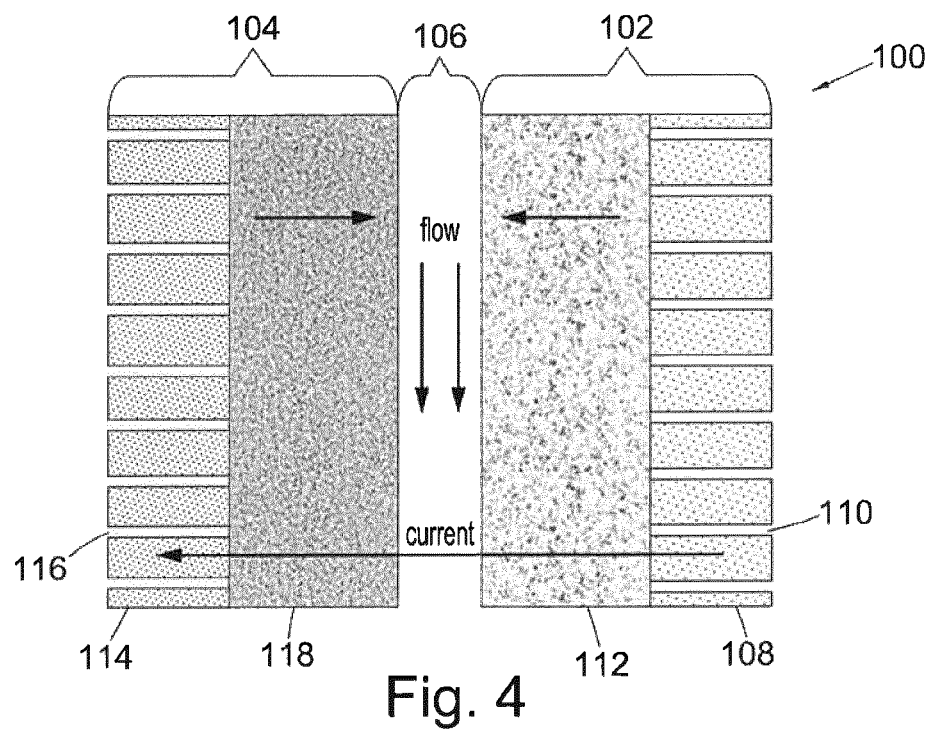
FIG. 4 is a schematic of an electroosmodialysis device.

The layered structure may also be used to provide an electroosmodialysis device 100 as shown in FIG. 4.

The electoosmodialysis device 100 may comprise a first layered structure 102 and a second layered structure 104. The first and second layered structures 102 and 104 may be layered structures as described above. The first and second layered structures 102, 104 are separated by a volume 106.

The first layered structure 102 comprises a first ion perm selective material layer 108 with openings 110 therein and a first electroosmotic layer 112.

The second layered structure 104 comprises a second ion perm selective material layer 114 with openings 116 therein and a second electroosmotic layer 118.

The sign of the ions to which the first ion perm selective material layer 108 is perm selective is opposite to the sign of the ions to which the second ion perm selective material layer 114 is perm selective. Accordingly (given that the fixed surface charges of the electroosmotic layer is the same sign as the sign of the ions to which its respective ion perm selective material layer is perm selective) the fixed surface charges of the electroosmotic layers 112, 118 are also opposite to each other.

The fixed surface charge of the electroosmotic layer is the opposite sign as the fixed charge of the respective ion perm selective material.

The two layered structures 102, 104 may therefore be regarded as a mirror image of each other.

When a voltage of a certain polarity is applied across the device 100 such that a current flows across the device, fluid will be transported by means of electroosmosis from the liquid surrounding the device 100 through one of the layered structures 102, 104, into the volume 106 between the layered structures 102, 104. A solution of reduced salinity will be pumped electroosmotically into the volume 106 thereby performing electrodialysis.

The invention claimed is:

1. A layered structure for pumping fluid by electroosmotic transport, the layered structure comprising:
   a first layer, wherein the first layer is made from an ion perm selective material having openings therein that permit the fluid to flow therethrough, and wherein the openings in the first layer that permit the fluid to flow therethrough create a porosity of less than 10%; and
   a second layer, wherein the second layer is an electroosmotic layer,
   wherein the layered structure has a net fluid flow direction that extends through the first layer and the second layer,
   wherein the layered structure has a region that permits fluid to flow in a direction that is non-parallel to a net fluid flow direction, and
   wherein the region is located between the first layer and the surface of the second layer that is furthest from the first layer.

2. A layered structure according to claim 1, wherein the second layer is on a downstream side of the first layer.

3. A layered structure as claimed in claim 1, wherein the openings in the first layer that permit the fluid to flow therethrough have a width dimension of 0.1 to 10 μm.

4. A layered structure as claimed in claim 3, wherein the openings in the first layer that permit the fluid to flow therethrough have a width dimension of 0.5 to 2 μm.

5. A layered structure as claimed in claim 1, wherein the second layer comprises the region that permits fluid to flow in a direction that is non-parallel to the net fluid flow direction.

6. A layered structure as claimed in claim 1, wherein the region that permits fluid to flow in a direction that is non-parallel to the net fluid flow direction is provided by a third layer located between the first layer and the second layer.

7. A layered structure as claimed in claim 1, wherein the region that permits fluid to flow in a direction that is non-parallel to the net fluid flow direction has a thickness that is at least 2 times the average distance between the openings of the first layer.

8. A layered structure as claimed in claim 1, wherein the electroosmotic layer has a fixed surface charge that is the same sign as the sign of the ions to which the material of the first layer is perm selective.

9. A layered structure as claimed in claim 1, wherein the first layer is provided on only one side of the second layer.

10. A layered structure as claimed in claim 1, wherein the layered structure is arranged so that, when electric current is passed through the layered structure in a first direction, the electrolyte concentration in the second layer will be decreased and, when electric current is passed through the layered structure in a second direction opposite to the first direction, the electrolyte concentration in the second layer will be increased.

11. A layered structure as claimed in claim 10, wherein the first electric current direction corresponds to the movement of ions, for which the material of the first layer is perm selective away from the second layer and towards the first layer.

12. A layered structure as claimed in claim 10, wherein when a given amount of charge flows in the first direction more electroosmotic transport of the fluid will occur through the layered structure than when the same amount of charge flows in the second direction.

13. A method of pumping a fluid through a layered structure by electroosmotic transport, the method comprising:
   providing a layered structure comprising:
      a first layer, wherein the first layer is made from an ion perm selective material having openings therein that permit the fluid to flow therethrough, and
      wherein the openings in the first layer that permit the fluid to flow therethrough create a porosity of less than 10%; and
      a second layer, wherein the second layer is an electroosmotic layer;
      wherein the layered structure has a net fluid flow direction that extends through the first layer and the second layer,
      wherein the layered structure has a region that permits fluid to flow in a direction that is non-parallel to a net fluid flow direction, and
      wherein the region is located between the first layer and the surface of the second layer that is furthest from the first layer; and
   applying an AC signal across the layered structure,
   wherein when a given amount of charge flows through the layered structure in a first direction more electroosmotic transport of the fluid occurs than when the same amount of charge flows through the layered structure in a second, opposite direction.

14. An electroosmodialysis apparatus, the apparatus comprising:
   a first layered structure comprising a first layer, wherein the first layer is made from an ion perm selective material having openings therein that permit the fluid to flow therethrough; and a second layer, wherein the second layer is an electroosmotic layer; and
   a second layered structure comprising a third layer, wherein the third layer is made from an ion perm selective material having openings therein that permit the fluid to flow therethrough; and a fourth layer, wherein the fourth layer is an electroosmotic layer; and
   a flow path between the first and second layered structures into which fluid is transported when a current is passed through the first and second layered structures.

15. An electroosmodialysis apparatus as claimed in claim 14, wherein the apparatus is arranged so that when a current is passed through the first and second layered structure fluid transported into the flow path is of a lower electrolyte concentration than fluid that has not been transported into the flow path.

16. An electroosmodialysis apparatus as claimed in claim 14, wherein the ion perm selective material of the first layer of the first layered structure and the ion perm selective material of the third layer of the second layered structure are of opposite polarity.

17. An electroosmodialysis apparatus as claimed in claim 14, wherein the second layer has a surface charge of the same sign as the charge to which the first layer is perm selective and the fourth layer has a surface charge of the same sign as the charge to which the third layer is perm selective.

18. A method of performing electroosmodialysis, the method comprising:
   providing an electroosmodialysis apparatus according to claim 14; and
   passing a current through the first and second layered structures to cause electroosmodialysis.

19. A layered structure for pumping fluid by electroosmotic transport, the layered structure comprising:
   a first layer, wherein the first layer is made from an ion perm selective material having openings therein that permit the fluid to flow therethrough; and
   a second layer, wherein the second layer is an electroosmotic layer,
   wherein the layered structure has a net fluid flow direction that extends through the first layer and the second layer,
   wherein the layered structure has a region that permits fluid to flow in a direction that is non-parallel to a net fluid flow direction, and
   wherein the region is located between the first layer and the surface of the second layer that is furthest from the first layer.

* * * * *